Figure 1:
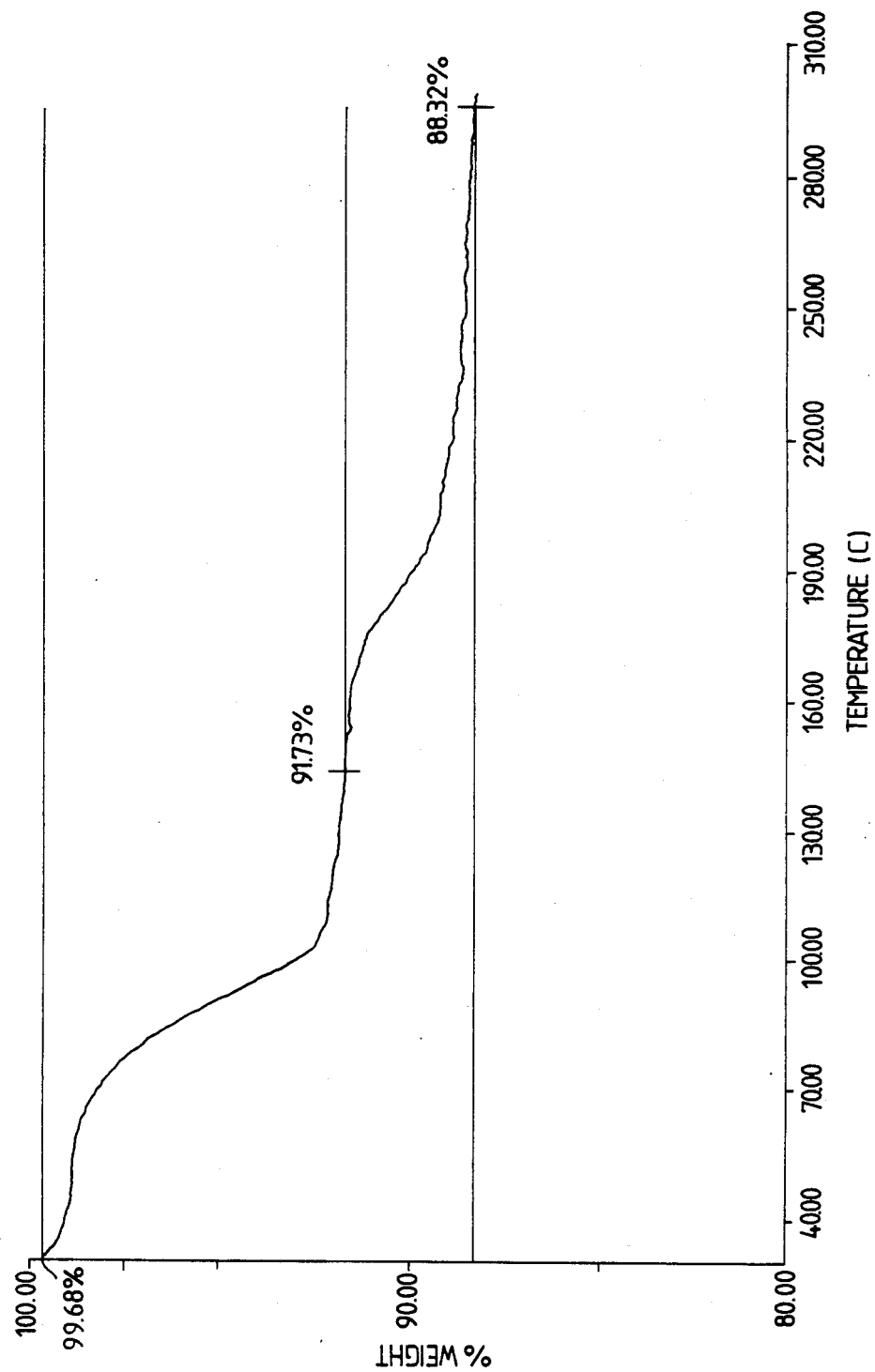

United States Patent [19]

Brown et al.

[11] Patent Number: 4,760,072
[45] Date of Patent: Jul. 26, 1988

[54] SOLID NEDOCROMIL SODIUM, USEFUL FOR THE REMOVAL OF OBSTRUCTED AIR PATHWAYS

[75] Inventors: Kenneth Brown; Andrew R. Clark, both of Loughborough; Richard Salliss, Holmes Chapel, all of England

[73] Assignee: Fisons, plc, Ipswich, England

[21] Appl. No.: 720,588

[22] Filed: Apr. 8, 1985

[30] Foreign Application Priority Data

Apr. 13, 1984 [GB] United Kingdom ............... 8409705
Sep. 19, 1984 [GB] United Kingdom ............... 8423634

[51] Int. Cl.$^4$ .................. A61K 31/35; C07D 491/052
[52] U.S. Cl. ..................... 514/291; 546/89; 546/92
[58] Field of Search ............... 546/89, 92; 514/291

[56] References Cited

U.S. PATENT DOCUMENTS 4,419,352 12/1983 Cox et al. ................... 546/92

FOREIGN PATENT DOCUMENTS 1112644 11/1981 Canada .......................... 546/92
2022078 6/1978 United Kingdom ............ 546/89

OTHER PUBLICATIONS

J. Labelled Compds. Radiopharm. 1985, 22(9) 883–889 (Eng).
Weissberger A. Technique of Org. Chem. vol. III part I, 1956 pp. 803–804, 513.
Robertson, G. R. Laboratory Practice of Org. Chem. 3rd Ed. pp. 113–114.
March, J. Adv. Org. Chem. pp. 804–805(2nd Ed).

Primary Examiner—Henry R. Jiles
Assistant Examiner—J. Richter
Attorney, Agent, or Firm—Marshall, O'Toole Gerstein, Murray & Bicknell

[57] ABSTRACT

There are described new forms of nedocromil sodium, methods of producing these new forms and pharmaceutical formulations, especially pressurized inhalation aerosol formulations, containing finely divided nedocromil sodium. The formulations are indicated for the treatment of reversible obstructive conditions of the airways.

15 Claims, 6 Drawing Sheets

SOLID NEDOCROMIL SODIUM, USEFUL FOR THE REMOVAL OF OBSTRUCTED AIR PATHWAYS

This invention relates to a new form of drug and pharmaceutical formulations containing it.

In British Patent Specification No. 2,022,078 a large number of pyranoquinolinone derivatives are described as being useful inter alia as prophylactic inhalation anti-asthmatics when administered as unit dosages of from 0.01 to 10 mg in admixture with coarse lactose. This patent specification also discloses the disodium salt of 9-ethyl-6,9-dihydro-4,6-dioxo-10-propyl-4H-pyrano[3,2-g]-quinoline-2,8-dicarboxylic acid, which salt is commonly known as nedocromil sodium or TILADE (TILADE is a registered trade mark).

It is further known to be desirable to make inhalation pharmaceuticals in the form of fine particles. These fine particles are conventionally made by grinding or milling larger sized particles of the pharmaceutical. Generally grinding and milling machines are extremely efficient and reduce the particle size of the material as far as they are capable in a single pass. Indeed the mass median diameter of product material can increase after a second pass through the grinder because some of the finest particles are lost to the system. We have also attempted to produce a material of very fine particle size by air classification of ground nedocromil sodium. However the product was of larger mean particle size than the starting material. We have thus found that with nedocromil sodium there is a very real difficulty in obtaining material which is of the optimum very fine particle size.

We have now found that nedocromil sodium is particularly suited to formulation as a pressurised aerosol formulation. We have also found new hydrated and fine particle forms of this compound.

According to the invention we provide a pharmaceutical formulation containing nedocromil sodium and a pharmaceutically acceptable liquefied gas aerosol propellant.

The nedocromil sodium is preferably finely divided, e.g. having a mass median diameter in the range 0.01 to 10 microns. We particularly prefer the nedocromil sodium to have a mass median diameter of less than 4 microns and especially of less than 3.0 microns and most preferably of less than 2.8 microns. We also prefer not more than 5% by weight of the particles to have a diameter of greater than 10 microns, and more preferably not less than 90% by weight of the particles to have a diameter of less than 6 microns. The nedocromil sodium is also preferably in a hydrated form (contrary to conventional teaching in the aerosol art) containing from 3 to 8%, preferably 3 to 6%, w/w water. Nedocromil sodium containing less than 5%, preferably 3 to 4% and most preferably about 3.5% w/w of water is new and represents a further feature of this invention. This material can be made by drying material of higher water content for, for example, 8 to 15 hours at 80° to 150° C., preferably 100° to 120° C. and especially at 105° C.

We prefer the composition to contain from 0.5 to 12%, more preferably from 0.5 to 10%, and most preferably from 0.5 to 5%, e.g. about 1 to 3.5% by weight of finely divided nedocromil sodium.

We have also found that nedocromil sodium can exist in two different forms. Thus there is a more stable and desired form A which is light yellow in colour. This form A of nedocromil sodium when in powder form containing 10% w/w of total water gives a yellow reading of below 2.0 and preferably of 0.8 to 1.8 using a Lovibond tintometer. Form A material has low readings, e.g. of less than 0.2 and preferably of zero, in the red and blue scales of the Lovibond tintometer.

Form A material also has bound water (i.e. between 3.0 and 4.0, e.g. about 3.5% w/w water) which cannot readily be removed by intensive drying at atmospheric pressure without destroying the compound. The presence of bound water is the most characteristic feature of form A material.

Form A material containing bound water can best be identified by thermogravimetric analysis in which the temperature of the material to be tested is increased at a constant rate and the change in weight of the sample is recorded against time. For material containing bound water the thermogravimetric trace is discontinuous and, for example, shows a plateau of substantially constant weight from about 100° to 160° C. when the temperatue of a 5 mg sample is increased at 20° C. per minute.

Form A material can also be identified in that the powder X-ray diffraction pattern shows marked and separated peaks between 27° and 34° diffraction angle, typically peaks at 28.5°, 29.5°-30.5° (doublet) and 32°-33° (doublet). These peaks indicate that the material is crystalline.

Form A material also shows a shoulder in its infra-red spectrum at 3500 cm$^{-1}$ when the total (i.e. bound plus unbound) water content of the material under test is 10% w/w.

In addition to the form A material there is a less desired form B which is of darker yellow colour, i.e. gives a yellow reading of 2.0 or more at 10% w/w total water using a Lovibond tintometer. Form B material also has no bound water and gives an essentially continuous trace on thermogravimetric analysis. The powder X-ray diffraction pattern for form B material also shows no marked peaks and is indicative that the material is amorphous.

Form B material also shows no shoulder at 3500 cms$^{-1}$ in its infra-red spectrum when the total water content of the material is 10% w/w.

Both forms A and B of the material when examined under the microscope appear to be crystalline, but the powder X-ray diffraction patterns indicate otherwise.

Form B material is less preferred in that it can, but does not necessarily, change spontaneously (sometimes after a very considerable time) to form A and in so doing can coalesce to produce hard and intractable lumps of particle size larger than the original material. Such a change, if it were to take place when the nedocromil sodium was in a pharmaceutical formulation, e.g. an aerosol formulation, could prove highly deleterious.

We have also found a method of producing nedocromil sodium in either form A or form B, and particularly a sub-form of form A which is suitable for grinding to produce very fine material.

According to the invention we further provide a process for the preparation of solid nedocromil sodium, preferably in a sub-form of form A suitable for milling or grinding, which comprises mixing an aqueous solution of nedocromil sodium with a water miscible precipitating solvent for the nedocromil sodium the ratio of nedocromil sodium to water to precipitating solvent being in the range 1 part by weight of nedocromil sodium: from 2 to 5, preferably about 3, parts by volume of water: from 10 to 25, preferably 16 to 20 and especially about 18 parts by volume of precipitating solvent.

Up to about 10, and preferably 3 to 8, e.g. 6, parts by volume of precipitating solvent per part by weight of nedocromil sodium may be present in the initial aqueous solution (prior to the mixing) and the remainder of the precipitating solvent may be used to precipitate the nedocromil sodium.

The precipitating solvent for the nedocromil sodium should be such that only a small amount of the nedocromil sodium will be dissolved in the final aqueous mixture containing the precipitating solvent. Suitable precipitating solvents include lower alkyl ketones, e.g. methyl ethyl ketone, and C2 to 6 alkanols, e.g. ethanol or most preferably propanol, especially isopropanol. Isopropanol is particularly advantageous in that it is a poor solvent for nedocromil sodium.

The aqueous solution preferably has a pH in the range 5.0 to 7.5.

The concentration of nedocromil sodium in the final mixture must be sufficiently low for the mixture to be adequately agitated, but should not be so low that the volumes involved and the losses of nedocromil sodium through solubility etc. become uneconomic.

We particularly prefer to use an aqueous solution of nedocromil sodium which is at a temperature of from 55° to 85° C., preferably about 65° to 75° C. and for the precipitating solvent to be at 25° C. or below before mixing.

The precipitating solvent is preferably mixed with, e.g. added to, the aqueous solution quickly, e.g. over a period of up to 20 minutes, and preferably over about 5 minutes. The mixing may also take place in a continuous process. Once the mixing has taken place the total mixture may be agitated, e.g. stirred, and preferably also cooled, to a temperature of from about 25° to 40° C., e.g. to about 25° C., for a further period, e.g. of about 1-5 hours, preferably 1.5 to 2.5 hours, to ensure that precipitation is as complete as possible. The use of lower temperatures, e.g. temperatures of the final mixture of below 25° C., lower proportions of solvent to water and longer stirring times tends to favour the production of viscous slurries which are difficult to handle and which contain form B of the nedocromil sodium. Thus we prefer to control the process so that the final mixture has a viscosity of less than 2,000, and more preferably less than 500 centipoise.

The nedocromil sodium may be separated from the aqueous solvent, e.g. by filtration, followed by washing with the precipitating solvent, and drying to constant weight, e.g. at 50° to 60°, for, for example, from 12 to 48 hours. The precipitating solvent, and any dissolved or entrained nedocromil sodium may, if desired, be recovered from the filtrate. Alternatively the filtrate may be recycled. Any form B material produced may also be recycled or may be converted to form A material by subjecting it to an atmosphere of high humidity, e.g. 50 to 80% humidity, and subsequently removing any excess water. The process may be carried out at ambient temperature, e.g. 15° to 30° C., over a period of, e.g. 5 to 24 hours. Any excess water may be removed by conventional drying techniques.

The dried product from the precipitation process can comprise crystalline needles of form A of nedocromil sodium having a breadth of from 1.5 to 3.5, and preferably 1.5 to 2.5, microns and a length to breadth ratio of up to 10:1. The nedocromil sodium in the form of the needles is new and forms a feature of this invention.

The new crystalline needles may be subjected to conventional grinding or milling techniques to provide nedocromil sodium of mass median diameter of less than 4 microns, e.g. of from 2 to 3 microns.

By mass median diameter we mean the diameter such that half the particulate mass is in particles of lesser diameter and half in particles of greater diameter. The mass median diameter is essentially a Stokes diameter and may be determined using a Joyce Loebl sedimentation disc centrifuge either in a two layer or line start photometric mode (Bagness J and Ottaway A. Proc. Soc. Analyt. Chem. Part 4, Vol 9, 1972 pages 83–86).

The nedocromil sodium of mass median diameter less than 4 microns when formulated as aerosol units and when the units are examined using a single stage liquid impinger (modification of that described in J. Pharm. Pharmac. 1973, 25, Suppl. 32P–36P) produces a greater dispersion than exactly analogous units containing nedocromil sodium of larger mass median diameter. The single stage liquid impinger samples the whole cloud delivered from the aerosol and separates it into two fractions by inertial impaction. The fraction of smaller particle size is less than 10 microns in aerodynamic diameter and represents material which is likely to penetrate into the deeper regions of the human airways.

By providing a greater proportion of fine particles of nedocromil sodium the invention enables a lower dosage of drug to be administered and/or for an equivalent amount of drug to produce a greater or longer lasting effect.

The precipitation process described above in addition to being capable of providing the nedocromil sodium in a form suitable for grinding also serves where necessary to remove water -, and precipitating solvent -, soluble impurities from the crude nedocromil sodium.

The fine nedocromil sodium is preferably dried thoroughly, e.g. to as close as possible to 3.5% w/w water, before it is incorporated into the liquefied propellant medium.

The liquefied propellant medium, and indeed the total formulation is preferably such that the nedocromil sodium does not dissolve therein to any substantial extent.

The liquefied propellant is preferably a gas at room temperature (20° C.) and atmospheric pressure i.e. it should have a boiling point below 20° C. at atmospheric pressure. The liquefied propellant should also be non-toxic. Among the suitable liquefied propellants which may be employed are dimethyl ether and alkanes containing up to five carbon atoms, e.g. butane or pentane, or a lower alkyl chloride, e.g. methyl, ethyl or propyl chlorides. The most suitable liquefied propellants are the fluorinated and fluorochlorinated lower alkanes such as are sold under the Registered Trade Mark 'Freon'. Mixtures of the above mentioned propellants may suitable be employed Examples of these propellants are dichlorodifluoromethane ('Propellant 12'), 1,2-dichlorotetrafluoroethane ('Propellant 114') trichloromonofluoromethane ('Propellant 11'), dichloromonofluoromethane ('Propellant 21'), monochlorodifluoromethane ('Propellant 22'), trichlorotrifluoroethane ('Propellant 113'), and monochlorotrifluoromethane ('Propellant 13'). Propellants with improved vapour pressure characteristics may be obtained by using certain mixtures of these compounds, e.g. 'Propellant 11' with 'Propellant 12', or 'Propellant 12' with 'Propellant 114'. For example, 'Propellant 12', which has a vapour pressure of about 570 k Pa (absolute) at 20° C. and 'Propellant 114', with a vapour pressure of about 180 k Pa (absolute) at 20° C., may be mixed in various proportions to form a propellant having a desired intermediate vapour pressure. We prefer compositions which do not contain trichloromonofluoromethane.

It is desirable that the vapour pressure of the propellant employed be between 380 and 500, and preferably between 410 and 470 k Pa (absolute) at 20° C. Such a propellant mixture is usable safely with metal containers. Other mixtures of 'Propellant 12' with 'Propellant 114', or of 'Propellant 12' with 'Propellant 11', or of 'Propellant 12' with 'Propellant 11' and Propellant 114' with absolute vapour pressures at 20° C. in the range 230 to 380 k Pa are usable safely with specially reinforced glass containers.

The composition may also contain a surface active agent. The surface active agent may be a liquid or solid non-ionic surface active agent or may be a solid anionic surface active agent. It is preferred to use the solid anionic surface active agent in the form of the sodium salt.

The preferred solid anionic surface active agent is sodium dioctyl-sulphosuccinate.

The amount of the surface active agent required is related to the solids content of the suspension and to the particle size of the solids. In general it is only necessary to use 5–15%, and preferably 5–8%, of the solid anionic surface active agent by weight of the solids content of the suspension. We have found that, under certain conditions, use of a solid anionic surface active agent gives a better dispersion of medicament when the composition is released from a pressurised pack than does the use of a liquid non-ionic surface active agent.

When a liquid, non-ionic surface-active agent is employed it should have an hydrophile-lipophile balance (HLB) ratio of less than 10. The HLB ratio is an empirical number which provides a guide to the surface-active properties of a surface-active agent. The lower the HLB ratio, the more lipophilic is the agent, and conversely, the higher the HLB ratio, the more hydrophilic is the agent. The HLB ratio is well known and understood by the colloid chemist and its method of determination is described by W C Griffin in the Journal of the Society of Cosmetic Chemists, Vol 1, No 5, pages 311–326 (1949). Preferably the surface-active agent employed should have an HLB ratio of 1 to 5. It is possible to employ mixtures of surface-active agents, the mixture having an HLB ratio within the prescribed range.

Those surface-active agents which are soluble or dispersible in the propellant are effective. The more propellant-soluble surface-active agents are the most effective.

We prefer the liquid non-ionic surface-active agent to comprise from 0.1 to 2%, and more preferably from 0.2 to 1%, by weight of the total composition. Such compositions tend to be more physically stable on storage.

Among the liquid non-ionic surface-active agents which may be employed are the esters or partial esters of fatty acids containing from 6 to 22 carbon atoms, such as caproic, octoic, lauric, palmitic, stearic, linoleic, linolenic, oleostearic and oleic acids with an aliphatic polyhydric alcohol or its cyclic anhydride such as, for example, ethylene glycol, glycerol, erythritol, arabitol, mannitol, sorbitol, the hexitol anhydrides derived from sorbitol (the sorbitan esters sold under the Registered Trade Mark 'Span') and the polyoxyethylene and polyoxypropylene derivatives of these esters. Mixed esters, such as mixed or natural glycerides, may be employed.

The preferred liquid non-ionic surface-active agents are the oleates of sorbitan, e.g. those sold under the Registered Trade Marks 'Arlacel C'(Sorbitan sesquioleate), 'Span 80'(Sorbitan monooleate) and 'Span 85'(Sorbitan trioleate). Specific examples of other liquid non-ionic surface-active agents which may be employed are sorbitan monolaurate, polyoxyethylene sorbitol tetraoleate, polyoxyethylene sorbitol pentaoleate, and polyoxypropylene mannitol dioleate. A solid non-ionic surface active agent which may be mentioned is lecithin, e.g. soya lecithin, a vegetable lecithin extracted from soya beans, but lecithin is not preferred.

We particularly prefer compositions containing a sorbitan or sorbitol ester, e.g. sorbitan trioleate, in a mixture of propellants 12 and 114. We prefer the ratio of propellant 12 to 114 to be in the range 2 to 1:1, and preferably about 1.5:1 by weight, i.e. we prefer an excess of propellant 12 over propellant 114.

As mentioned above contrary to the conventional teaching in the medicinal aerosol art, we prefer to use the nedocromil sodium in hydrated form. We also prefer the total water content of the formulation to be in the range of 500 to 3,500 ppm. The formulation when initially made preferably has a water content at the lower end of this range, but the water content tends to rise on storage.

Pressurised aerosol formulations of the nedocromil sodium are advantageous in that they are more convenient for the patient to use, and that lower dosages of nedocromil sodium can be used (thus avoiding any possible side-effects) when compared to so-called dry powder (e.g. lactose) formulations of the nedocromil sodium.

We prefer packages containing from about 8 to 30 ml of composition, e.g. a conventional aerosol pressure pack of 10 ml. The pack preferably has a valve adapted to deliver unit dosages of between 0.025 and 0.25 mls, and preferably 0.05 or 0.1 mls, of composition. We prefer the valve to deliver 1, 2 or 4 mg of nedocromil sodium and unit doses of these quantities of the drug are provided.

The compositions of the invention may be made by mixing the various components at a temperature and pressure at which the propellant is in the liquid phase and the nedocromil sodium is in the solid phase.

In producing the compositions and packages of the invention, a container equipped with a valve is filled with a propellant containing the finely-divided nedocromil sodium in suspension. A container may first be charged with a weighed amount of dry nedocromil sodium which has been ground to a predetermined particle size, or with a slurry of powder in the cooled liquid propellant. A container may also be filled by introducing powder and propellant by the normal cold filling method, or a slurry of the powder in that component of the propellant which boils above room temperature may be placed in the container, the valve sealed in place, and the balance of the propellant may be introduced by pressure filling through the valve nozzle. As a further alternative a bulk of the total composition may be made and portions of this bulk composition may be filled into the container through the valve. Throughout the preparation of the product care is desirably exercised to minimise the absorption of moisture. On operating the valve, the powder will be dispensed in a stream of propellant, which will vaporise providing an aerosol of dry powder.

The compositions of the invention may be used in the treatment of a number of allergic conditions in mammals, e.g. the inhalation treatment of reversible obstructive conditions of the airways, such as asthma or allergic rhinitis (hay fever). The treatment is preferably by oral or nasal inhalation and is preferably treatment of man.

The invention is illustrated, but in no way limited by the following Examples.

EXAMPLE 1

Method

The sorbitan ester is dispersed in up to half the propellant 12 at −40° C. while stirring with a high dispersion mixer. The nedocromil sodium is added to the resulting dispersion and disperses in it very readily. The balance of the propellant 12 is then added at −50° C., followed by the propellant 114 also cooled to −50° C. The resulting mixtures are then filled into vials onto which valves, e.g. metering valves, are subsequently crimped.

| Ingredients | |
|---|---|
| Nedocromil sodium (form A) containing 3.5% bound water, mass median diameter less than 3 microns | 0.270 |
| Sorbitan trioleate | 0.091 |
| Propellant 114 | 7.099 |
| Propellant 12 | 10.649 |
| | 18.109 |

Stability

Batches of vials fitted with metering valves and containing the above formulations were stored at 5° C., 25° C. and 37° C. respectively for a period of 18 months. No change in (a) the amount of nedocromil sodium dispensed per shot, (b) the content of fine particles in the cloud or (c) the crystal size of the nedocromil sodium was observed over the period of observation.

EXAMPLE 2

Twenty grams of the nedocromil sodium were dissolved in 60 ml of deionised water and 180 ml of isopropyl alcohol by heating to reflux at 81° C. To this solution was then added a further 190 ml of isopropanol (temperature 25° C.) with agitation. The crystal slurry was then cooled in air, maintaining agitation, until a temperature of 25° C. had been reached. The crystals were then filtered on a Buchner filter, using a terylene filter cloth. The filter cake was washed with a displacement volume of isopropanol and filtered further. The cake was then dried in an oven, at atmospheric pressure and 60° C., to constant weight.

EXAMPLE 3

1 Kg of nedocromil sodium is dissolved in three liters of deionised water and six liters of isopropanol at 30° C., and the mixture is then heated to reflux (at 81° C.) with agitation to ensure dissolution. The resulting solution is cooled slightly to about 75° C. and then added to another 12.5 liters of isopropanol at a temperature of about −8° C., as quickly as possible. This precipitates out most of the nedocromil sodium and produces a slurry. This slurry is then stirred and cooled to 25° C. over about an hour, to precipitate out further material. The temperature of the slurry is kept at 25° C. and the slurry filtered as soon as possible to remove the mother liquor, and then dried to constant weight at 60° C.

EXAMPLE 4

Twenty grams of nedocromil sodium were mixed with 60 ml of de-ionised water and 180 ml isopropanol in a 700 ml reaction flask. The mixture was agitated with an anchor-type stirrer at 120 rpm, and heated to its boiling point at around 80° C. The flask was fitted with a water-cooled condenser to prevent escape of isopropanol vapour. The resulting solution was refluxed for about 10 minutes to ensure complete dissolution. The hot solution of nedocromil sodium was then cooled to 75° C. and then added in about 20 seconds to 190 ml of isopropanol at 8° C. The resulting slurry was stirred with the anchor agitator and cooled to 25° C. in the reaction flask. The time taken for cooling was about 45 minutes and throughout this time the crystal slurry remained as the pale yellow, free flowing form. The slurry was then filtered on a Buchner filter using terylene filter cloth, washed with about 50 ml isopropanol and dried in an oven at 60° C. to constant weight. The resulting dried material was Apex milled, and micronised in a fluid energy mill. The nedocromil sodium was then subjected to particle size analysis by the Joyce-Loebl disc centrifuge method.

In four laboratory precipitations using this method particles of mass mean diameter 2.5, 2.5, 2.8 and 2.8 microns were produced, and these gave aerosol dispersions of 26% and 23% from a 50 microliter valve using the formulation described in Example 1. The dispersion was measured with a single stage liquid impinger.

EXAMPLE 5

Twenty grams of crude nedocromil sodium were mixed with 60 ml of deionised water and 120 ml isopropanol in a 700 ml flask. The mixture was agitated with an anchor-type stirrer at 120 rpm, and heated to its boiling point. The solution was refluxed for about 10 minutes to ensure complete dissolution, and then cooled to 75° C. At this temperature the solution was added to a further 250 ml of isopropanol which was at a temperature of about −8° C. The resulting slurry was stirred with an anchor agitator as in Example 4 and cooled to 25° in air. At this temperature the slurry, which was pale yellow and free flowing, was filtered on the Buchner filter, washed and dried.

EXAMPLE 6

Twenty grams of crude nedocromil sodium were mixed with 60 ml of deionised water and 180 ml of isopropyl alcohol in a 700 ml reaction flask. The mixture was agitated with an anchor-type agitator at 120 rpm and heated to boiling point at about 80° C. The solution was refluxed for 10 minutes and then cooled to 75° C. To it was then added a further 140 ml isopropanol at 15° C. The resulting mixture had a temperature of 66° C. The resulting slurry was then agitated as in Example 4 and cooled in an ice/salt/isopropanol bath to 22° C. in 30 minutes. A thick, bright yellow slurry was produced which had a viscosity of about 20,000 centipoise. This slurry was filtered, washed and dried as in Example 4. The material was shown to contain no tightly bound water, i.e. to be form B.

Example 6 illustrates the production of the undesirable thick crystal slurry; i.e. using less isopropanol in the solvent mix and cooling quickly in an ice bath to below 25° C. Examples 2 to 5 show methods of producing nedocromil sodium in form A.

EXAMPLE 7

(a) Two samples of about 5 mg of nedocromil sodium were submitted to thermogravimetric analysis at a scan rate of 20° C. per minute.

We claim:

1. Solid nedocromil sodium which is cystalline and which contains bound water as determined by thermogravimetric analysis.

2. Solid nedocromil sodium according to claim 1 containing between 3.0 and 4.0% w/w bound water.

3. Solid nedocromil sodium according to claim 1 containing 3.5% bound water.

4. Nedocromil sodium according to claim 2 in powder form and having a Lovibond yellow reading of below 2.0 when containing 10% w/w water.

5. Nedocromil sodium according to claim 4 having a Lovibond yellow reading of between 0.8 and 1.8.

6. Nedocromil sodium according to claim 1, wherein the powder X-ray diffraction pattern shows that the material is crystalline.

7. Nedocromil sodium according to claim 1 whose infra-red spectrum shows a shoulder at 3500 cms$^{-1}$ when its total water content is 10% w/w.

8. An inhalation formulation for treatment of a reversible obstructive condition of the airways comprising a pharmaceutically acceptable liquefied gas propellant containing nedocromil sodium according to claim 1 having a mass median diameter of less than 4 microns in a proportion which is effective for treatment of said condition.

9. A formulation according to claim 8, wherein not more than 5% by weight of the particles has a diameter of greater than 10 microns and not less than 90% by weight of the particles has a diameter of less than 6 microns.

10. A formulation according to claim 8, containing from 0.5 to 10% by weight of finely divided nedocromil sodium.

11. A formulation according to claim 8 comprising a mixture of propellants 12 and 114, the proportion of propellant 12 to 114 being in the range 2 to 1:1 by weight.

12. A formulation according to claim 11 containing sorbitan trioleate.

13. Nedocromil sodium in accordance with claim 1 the form of needles having a breadth of 1.5 to 3.5 microns and a length to breadth ratio of up to 10:1.

14. Nedocromil sodium according to claim 13 having a breadth of 1.5 to 2.5 microns.

15. A method of treatment of a reversible obstructive condition of the airways in a mammal which comprises administering by inhalation an effective amount of solid nedocromil sodium according to claim 1 to a mammal suffering from said condition.

* * * * *

UNITED STATES PATENT AND TRADEMARK OFFICE
CERTIFICATE OF CORRECTION

PATENT NO. : 4,760,072
DATED : July 26, 1988
INVENTOR(S) : Kenneth Brown et al.

It is certified that error appears in the above-identified patent and that said Letters Patent is hereby corrected as shown below:

Column 9, line 7, after "per minute." insert

Figure 2:
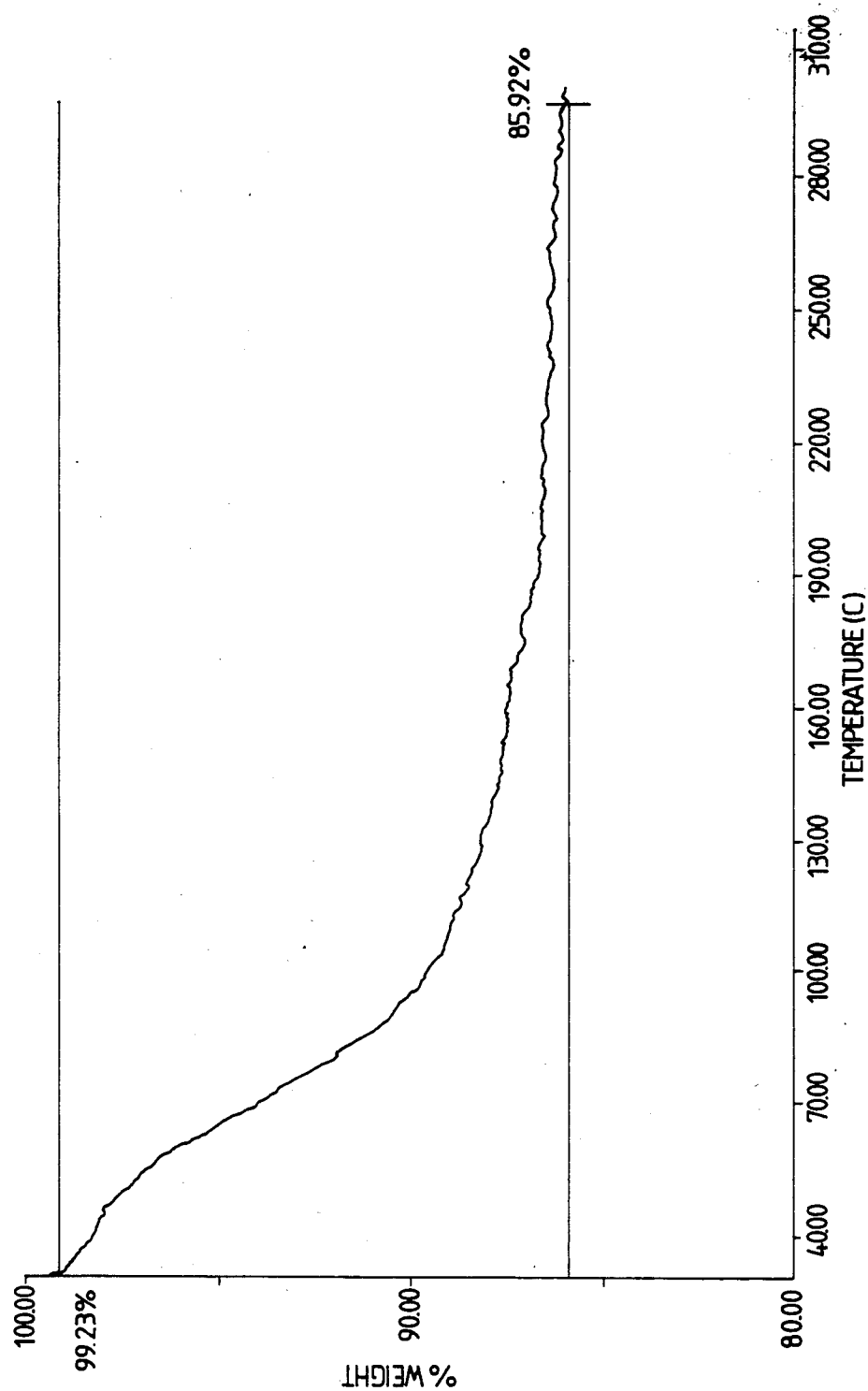

--Figure 1 shows the trace from material in form A and figure 2 shows the trace from material in form B.

Figure 3:
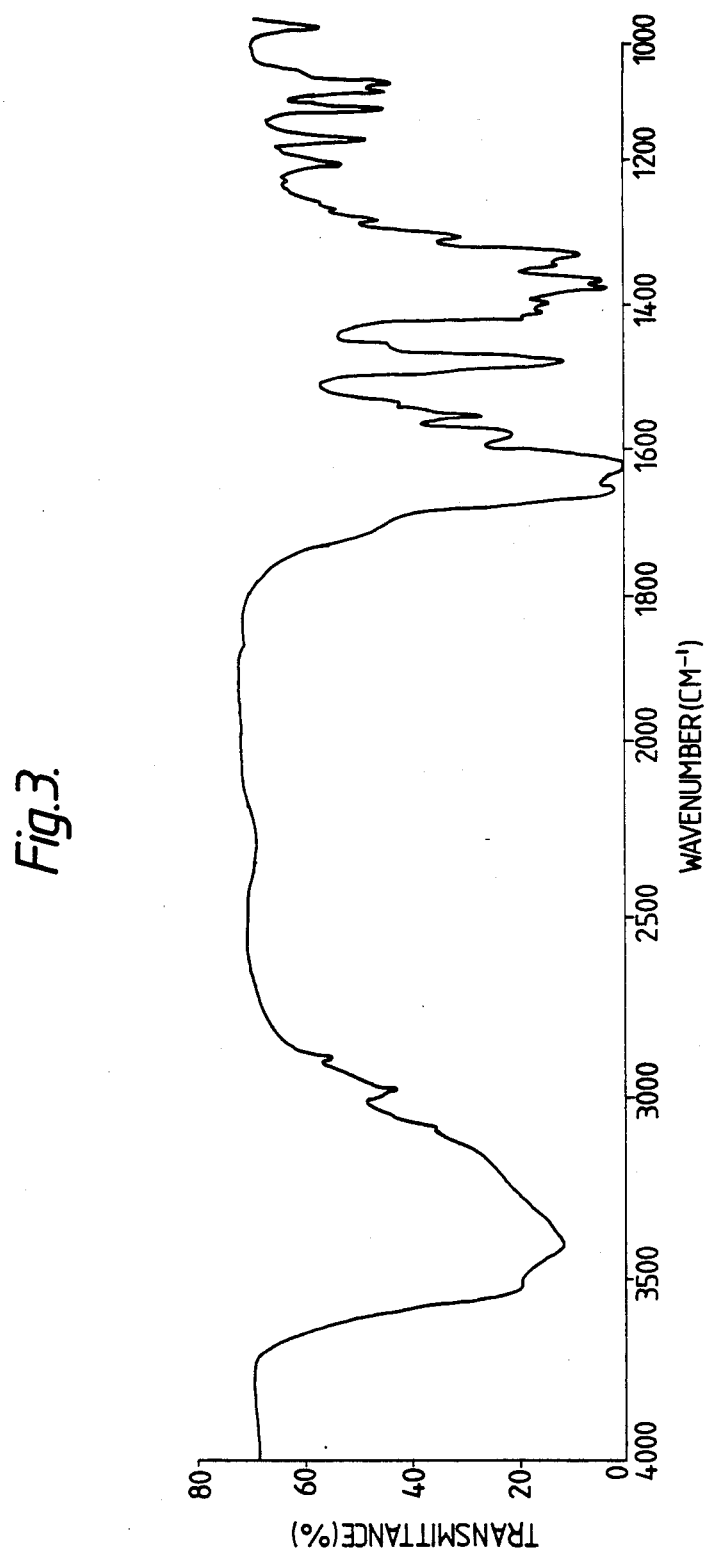
Figure 4:
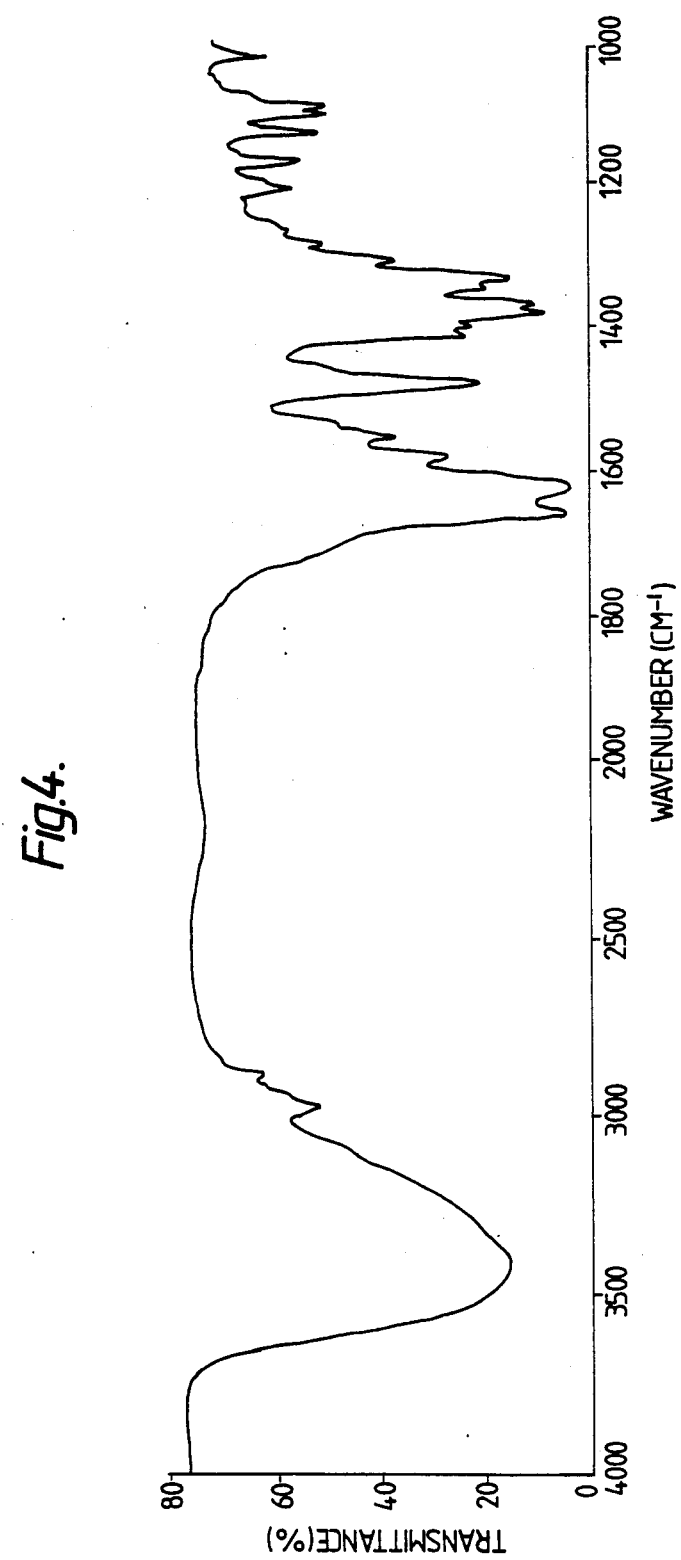

(b) The infra-red spectra for forms A and B of nedocromil sodium containing 10% w/w water are shown respectively in Figures 3 and 4.

Figure 5:
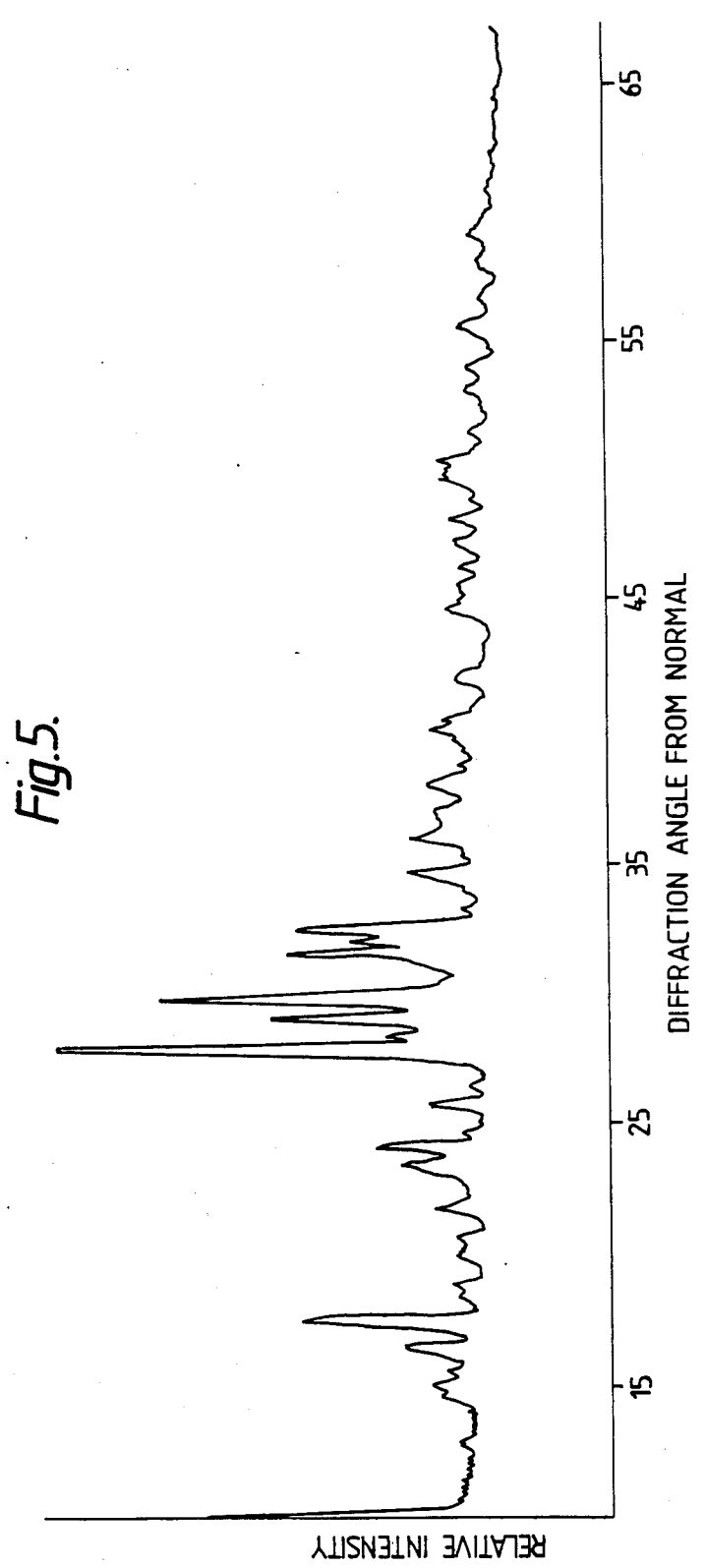
Figure 6:
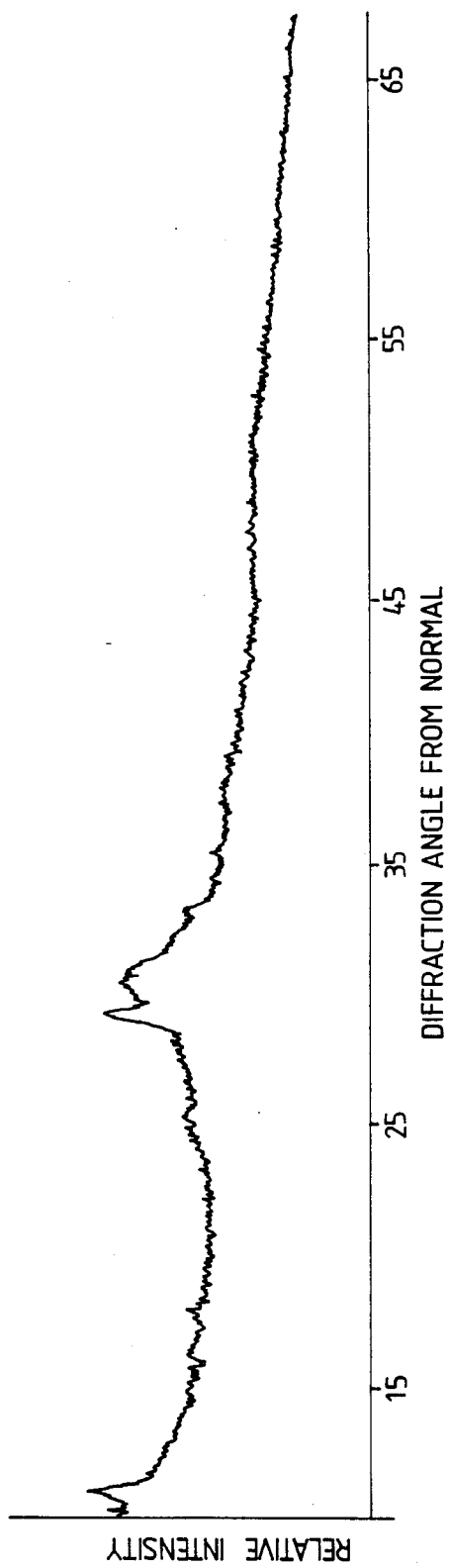

(c) The powder X-ray spectra for forms A and B are shown respectively in Figures 5 and 6.--

Signed and Sealed this

Seventeenth Day of October, 1989

Attest:

DONALD J. QUIGG

Attesting Officer     Commissioner of Patents and Trademarks